United States Patent [19]

Hino et al.

[11] Patent Number: 5,821,382
[45] Date of Patent: Oct. 13, 1998

[54] METHOD FOR MANUFACTURING THIOL COMPOUNDS

[75] Inventors: Youichi Hino; Ryuichi Ishikawa, both of Sakai; Norihiro Wakao, Suita, all of Japan

[73] Assignee: Nippon Shokubai Co., Ltd., Osaka, Japan

[21] Appl. No.: 945,087

[22] PCT Filed: Feb. 28, 1997

[86] PCT No.: PCT/JP97/00635

§ 371 Date: Oct. 16, 1997

§ 102(e) Date: Oct. 16, 1997

[87] PCT Pub. No.: WO97/33865

PCT Pub. Date: Sep. 18, 1997

[30] Foreign Application Priority Data

Mar. 11, 1996 [JP] Japan ................................ 8-53513

[51] Int. Cl.$^6$ .................................................. C07C 69/34
[52] U.S. Cl. .......................................... 560/146; 562/606
[58] Field of Search ............................... 560/147; 562/606

[56] References Cited

U.S. PATENT DOCUMENTS

| 5,008,432 | 4/1991 | Roberts ................................ 558/436 |
| 5,157,147 | 10/1992 | Chisholm et al. ....................... 560/147 |

FOREIGN PATENT DOCUMENTS

| 52-36623 A | 3/1977 | Japan . |
| 57-48155 B | 10/1982 | Japan . |
| 58-54138 B | 12/1983 | Japan . |
| 59-186955 A | 10/1984 | Japan . |
| 61-254555 A | 11/1986 | Japan . |

*Primary Examiner*—Samuel Barts
*Attorney, Agent, or Firm*—Kubovcik & Kubovcik

[57] ABSTRACT

In order to manufacture a thiol compound by causing reaction between an unsaturated compound and hydrogen sulfide, the unsaturated compound and the thiol compound being expressed by following formulas (1) and (2), respectively:

$$CH_2=CR^1-COOR^2 \quad (1)$$

$$HS-CH_2-CHR^1-COOR^2 \quad (2)$$

where $R^1$ represents a hydrogen atom or a methyl group, and $R^2$ represents a hydrogen atom or a hydrocarbon group with 1 to 18 carbon atoms, (i) at least one nitrogen containing compound which is selected from the group consisting of amide compounds each having an amide group without a substituent, amide compounds each having an amide group whose nitrogen atom has a substituent hydrocarbon group with 1 to 6 carbon atoms, urea compounds each having an ureylene group without a substituent, and urea compounds in each of which at least one of two nitrogen atoms (N, N') has a substituent hydrocarbon group with 1 to 6 carbon atoms, and (ii) either a polysulfide compound or sulfur, or the both, are made to coexist in a system of reaction.

13 Claims, 1 Drawing Sheet

FIG. 1

METHOD FOR MANUFACTURING THIOL COMPOUNDS

TECHNICAL FIELD

The present invention relates to a method for manufacturing thiol compounds by causing reaction between (1) unsaturated compounds such as unsaturated esters or unsaturated acids and (2) hydrogen sulfide.

The thiol compounds are chemical substance of great use which are widely utilized as material of pharmaceutical products, agricultural chemicals, and various kinds of industrial chemical products.

BACKGROUND ART

The following methods have been known as methods for manufacturing 3-mercapto-propionic ester, which is one of thiol compounds, by causing reaction between, for example, (1) acrylic ester, which is one of unsaturated esters, and (2) hydrogen sulfide.

The Japanese Publication for Laid-Open Patent Application No. 62-63526/1987 (Tokukaisho 62-63526) discloses a method wherein magnesium oxide or an anionic exchange resin is used as catalyst in the system of reaction. However, this method requires, as conditions for the reaction, a reaction pressure of not lower than 13 atm, and large excess of hydrogen sulfide, for example, the molar ratio of 6:1 for hydrogen sulfide and acrylic ester. This leads to an excessive investment in plant and equipment, and therefore the foregoing method does not bring about satisfactory results from a viewpoint of industrial productivity.

The Japanese Examined Patent Publication No. 57-48155/1982 (Tokukosho 57-48155) discloses a method wherein 3-mercapto-propionic ester and/or thiodipropionic ester, which are reaction products, is/are used as solvent in the above system of reaction. By this method, 3-mercapto-propionic ester is obtained under a reaction pressure of about 10 atm at a relatively high yield. However, the foregoing method has a disadvantage in that excess of hydrogen sulfide with respect to acrylic ester should be increased in order to obtain 3-mercapto-propionic ester at a high selectivity and at a high yield.

Therefore, a method wherein polythiodipropionic ester such as dithiodipropionic ester is used as solvent in the aforementioned system of reaction, to raise the yield of 3-mercapto-propionic ester, is disclosed, for example, in the Japanese Examined Patent Publications No. 59-34181/1984 (Tokukosho 59-34181) and No. 63-19509/1988 (Tokukosho 63-19509), and the Japanese Publication for Laid-Open Patent Application No. 4-273851/1992 (Tokukaihei 4-273851). In addition, a method wherein sulfur is used is disclosed in the Japanese Examined Patent Publication No. 58-54138/1983 (Tokukosho 58-54138).

However, by none of the aforementioned methods, a satisfactory result can be obtained in respect of the lowering of the reaction pressure and the improvement of the yield. In other words, by none of the aforementioned methods, the reaction pressure can be satisfactorily lowered while the yield can be satisfactorily improved. Note that the Japanese Examined Patent Publication No. 63-35621/1988 (Tokukosho 63-35621) discloses a method wherein an amide compound having a specific structure is used as a solvent in the above system of reaction. Though by this method it is easy to recover the solvent after the reaction, the results obtained by this method are not satisfactory from a viewpoint of industrial productivity, since the yield of 3-mercapto-propionic ester is relatively low.

Therefore, a manufacturing method whereby the reaction pressure is further lowered and the selectivity and the yield are further improved is demanded, from a viewpoint of industrial productivity.

The present invention was made in light of the aforementioned problems of the conventional methods, and the object of the present invention is to provide a method whereby a thiol compound can be produced at a high selectivity and a high yield by smooth reaction between (1) an unsaturated compound such as an unsaturated ester or an unsaturated acid and (2) hydrogen sulfide.

DISCLOSURE OF THE INVENTION

As a result of eager study by the inventors on a method for manufacturing thiol compounds, it was found that reaction between an unsaturated compound and hydrogen sulfide was smoothly caused by causing (1) a nitrogen containing compound which has a specific structure and (2) polysulfide compound which has a specific structure and/or sulfur to coexist in a system of reaction, and that by this reaction a thiol compound could be produced at a high selectivity and a high yield. The present invention was completed based on this finding.

More specifically, to achieve the aforementioned object, the method of the present invention for manufacturing a thiol compound is characterized in comprising the step of causing reaction between an unsaturated compound and hydrogen sulfide so as to produce the thiol compound, the unsaturated compound and the thiol compound being expressed by following formulas (1) and (2), respectively:

$$CH_2=CR^1-COOR^2 \qquad (1)$$

$$HS-CH_2-CHR^1-COOR^2 \qquad (2)$$

where $R^1$ represents a hydrogen atom or a methyl group, and $R^2$ represents a hydrogen atom or a hydrocarbon group with 1 to 18 carbon atoms, wherein (i) at least one nitrogen containing compound which is selected from the group consisting of amide compounds each having an amide group without a substituent, amide compounds each having an amide group whose nitrogen atom has a substituent hydrocarbon group with 1 to 6 carbon atoms, urea compounds each having an ureylene group without a substituent, and urea compounds in each of which at least one of two nitrogen atoms (N, N') has a substituent hydrocarbon group with 1 to 6 carbon atoms, and (ii) either a polysulfide compound or sulfur, or the both, coexist in a system of reaction, the polysulfide compound being expressed by a following formula (3):

$$R^4OOC-CHR^3-CH_2-S_x-CH_2-CHR^3-COOR^4 \qquad (3)$$

where $R^3$ represents a hydrogen atom or a methyl group, $R^4$ represents a hydrogen atom or a hydrocarbon group with 1 to 18 carbon atoms, and x represents an integral number of 2 to 5.

Besides, the method of the present invention for manufacturing the thiol compound is characterized in that x in the formula (3) is 2. Moreover, the method of the present invention for manufacturing the thiol compound is characterized in that (i) the nitrogen containing compound whose weight is in a range of 0.01 to 5 times a weight of the unsaturated compound and (ii) the polysulfide compound whose weight is in a range of 0.02 to 5 times the weight of the unsaturated compound and/or the sulfur whose weight is in a range of 0.002 to 0.1 time the weight of the unsaturated compound, coexist in the system of reaction. Furthermore, the method of the present invention for manufacturing the thiol compound is characterized in that the reaction is caused under the presence of a basic catalyst.

By the aforementioned method, the unsaturated compound and hydrogen sulfide are caused to smoothly react with each other, and the thiol compound can be obtained at a high selectivity and a high yield, as compared with the case where only either the nitrogen containing compound, or the polysulfide compound and/or sulfur, is supplied to the system of reaction. In short, as compared with this case, the selectivity and the yield of the thiol compound can be remarkably improved.

For a fuller understanding of the nature and advantages of the invention, reference should be made to the ensuing detailed description taken in conjunction with the accompanying drawings.

DESCRIPTION OF THE PREFERRED EMBODIMENTS

The following description will explain the present invention in detail.

The method of the present invention for manufacturing thiol compounds expressed by the foregoing formula (2) is a method wherein (a) a nitrogen containing compound having a specific structure and (b) a polysulfide compound expressed by the formula (3) and/or sulfur are caused to coexist in a system of reaction so as to cause reaction between an unsaturated compound expressed by the foregoing formula (1) and hydrogen sulfide.

The unsaturated compounds expressed by the formula (1), which are used as materials in the present invention, are compounds each of which has (i) a substituent group represented by $R^1$ in the formula, which is either a hydrogen atom or a methyl group, and (ii) a substituent group represented by $R^2$ in the formula, which is a hydrogen atom or a hydrocarbon group with 1 to 18 carbon atoms. Examples of such a hydrocarbon group with 1 to 18 carbon atoms are: saturated aliphatic hydrocarbon groups such as a methyl group, an ethyl group, a butyl group, a 2-ethylhexyl group, a cyclohexyl group, a lauryl group, and a stearyle group; unsaturated aliphatic hydrocarbon groups such as an aryl group, and a metharyl group; and aromatic hydrocarbon groups such as a phenyl group.

Therefore, the following are given as examples of the unsaturated compound:

acrylic acid, and methacrylic acid; and unsaturated esters such as methyl acrylate, ethyl acrylate, butyl acrylate, 2-ethylhexyl acrylate, cyclohexyl acrylate, lauryl acrylate, stearyle acrylate, aryl acrylate, phenyl acrylate, methyl methacrylate, ethyl methacrylate, butyl methacrylate, 2-ethylhexyl methacrylate, cyclohexyl methacrylate, lauryl methacrylate, stearyle methacrylate, metharyl methacrylate, and phenyl methacrylate.

The method of the present invention makes it possible to obtain, from the aforementioned unsaturated compounds, thiol compounds expressed by the aforementioned formula (2), which respectively correspond to the unsaturated compounds used. 3-mercapto-propionic ester, which is obtained in the case where acrylic ester is used as the unsaturated compound, is particularly important as an industrial material.

As hydrogen sulfide used as a material in the present invention, an industrial-use hydrogen sulfide containing an impurity such as carbon dioxide or water can be used, let alone purified hydrogen sulfide available in stores. The excess of hydrogen sulfide, which is recovered after the reaction, is of course repeatedly used. Note that the industrial-use hydrogen sulfide can be easily and inexpensively obtained through an industrial process, for example, from a desulfurizing process in oil refining.

As to a usage of hydrogen sulfide, it is preferable that 1.0 to 5.0 moles of hydrogen sulfide is used with respect to 1 mole of the unsaturated compound (that is, a molar ratio of hydrogen sulfide/unsaturated compound falls in a range of 1 through 5), and it is more preferable that 1.0 to 3.0 moles of hydrogen sulfide is used with respect to 1 mole of the unsaturated compound (that is, a molar ratio of hydrogen sulfide/unsaturated compound falls in a range of 1 through 3). In the case where hydrogen sulfide is excessively used with respect to the unsaturated compound, the selectivity from the unsaturated compound to the thiol compound is improved. But, in the case where the used hydrogen sulfide exceeds 5 moles with respective to 1 mole of the unsaturated compound, the selectivity is less improved, whereas an amount of non-reacted hydrogen sulfide recovered after the reaction increases. Therefore, this is not preferable. To the contrary, in the case where less than 1 mole of hydrogen sulfide is used with respect to 1 mole of unsaturated compound, reaction between the unsaturated compound and the thiol compound more likely occurs, thereby causing the yield to become lower. Therefore, this is not preferable, either.

A nitrogen containing compound which is to coexist in the system of reaction in the present invention is at least one compound selected from the group consisting of: amide compounds each having an amide group without a substituent (hereinafter referred to as amide compounds without substituents); amide compounds each having an amide group whose nitrogen atom has a substituent hydrocarbon group with 1 to 6 carbon atoms (hereinafter referred to as amide compounds with substituents); urea compounds each having an ureylene group without a substituent (hereinafter referred to as urea compounds without substituents); and urea compounds in each of which at least one of two nitrogen atoms (N, N') has a substituent hydrocarbon group with 1 to 6 carbon atoms (hereinafter referred to as urea compounds with substituents). The following are examples of the hydrocarbon group with 1 to 6 carbon atoms: a methyl group, an ethyl group, a butyl group, a cyclohexyl group, and a phenyl group.

Examples of the amide compounds without substituents are: chain amide compounds such as formamide, and acetamide; and cyclic amide compounds such as 2-pyrrolidone.

As the amide compounds with substituents, the following compounds are taken as examples: chain amide compounds such as N,N-dimethyl formamide, N,N-diethyl formamide, N,N-dimethyl acetamide, and N,N-diethyl acetamide; and cyclic amide compounds such as N-methyl-2-pyrrolidone, and N-ethyl-2-pyrrolidone.

As the urea compound without substituents, chain compounds such as urea, and cyclic compounds such as ethylene urea (2-imidazolidinone) are taken as examples.

Examples of the urea compounds with substituents are: chain compounds such as 1,1,3,3-tetramethyl urea; and cyclic compounds such as 1-methyl-2-imidazolidinone, 1,3-dimethyl-2-imidazolidinone, and 1,3-diethyl-2-imidazolidinone.

One of these nitrogen containing compounds may be used, or, not less than two of these nitrogen containing compounds may be used. An amount of the nitrogen containing compound present in the system of reaction, that is, a usage of the nitrogen containing compound, is not specifically limited, but it is preferable that weight of the nitrogen containing compound falls in a range of 0.01 to 5 times the weight of the unsaturated compound, and it is more preferable that the weight of the nitrogen containing compound falls in a range of 0.05 to 3 times the weight of the unsaturated compound. In the case where the usage of the nitrogen containing compound exceeds or falls short of the aforementioned range, a thiol compound cannot be obtained at a high selectivity and a high yield, and the productivity drops.

The polysulfide compounds (polythionic compounds), expressed by the foregoing formula (3), which should coexist in the system of reaction in the present invention, are chemical compounds in each of which a substituent group represented by $R^3$ in the formula is a hydrogen atom or a methyl group, a substituent group represented by $R^4$ in the formula is a hydrogen atom or a hydrocarbon group with 1 to 18 carbon atoms, and x is an integral number of 2 to 5. A polysulfide compound in which x is 2, that is, disulfide compound, is particularly preferable since it is easy to handle and has an excellent multiplier effect which is achieved by coexistence. Examples of the hydrocarbon group having 1 to 18 carbon atoms are: saturated aliphatic hydrocarbon groups such as a methyl group, an ethyl group, a butyl group, a 2-ethylhexyl group, a cyclohexyl group, a lauryl group, and a stearyle group; unsaturated aliphatic hydrocarbon groups such as an aryl group, and a metharyl group; and aromatic hydrocarbon groups such as a phenyl group.

Given as examples of the polysulfide compounds are dithiodipropionic acid, methyl dithiodipropionate, ethyl dithiodipropionate, trithiodipropionic acid, methyl trithiodipropionate, and ethyl trithiodipropionate. Besides, among the above, particularly preferable is a polysulfide compound in which the substituent group represented by $R^3$ is equal to the substituent group represented by $R^1$ in the unsaturated compound, and the substituent group represented by $R^4$ is equal to the substituent group represented by $R^2$ in the unsaturated compound. In other words, a polysulfide compound which has a structure corresponding to the structure of the unsaturated compound is particularly preferable.

An amount of the polysulfide compound present in the system of reaction, that is, a usage of the polysulfide compound, is not specifically limited, but it is preferable that weight of the polysulfide compound falls in a range of 0.02 to 5 times the weight of the unsaturated compound, and it is more preferable that the weight of the polysulfide compound falls in a range of 0.05 to 3 times the weight of the unsaturated compound. In the case where the usage of the polysulfide compound exceeds or falls short of the aforementioned range, a thiol compound cannot be obtained at a high selectivity and a high yield, and the productivity drops.

It is needless to say that refined sulfur available at stores can be used as sulfur to coexist in the system of reaction in the present invention. In addition, crude sulfur (for industrial use) can be also used. It should be noted that the crude sulfur can be easily and inexpensively obtained through an industrial process, for example, from a desulfurizing process in oil refining, or from a waste gas recovering process in sulfur ore smelting.

An amount of sulfur present in the system of reaction, that is, a usage of sulfur, is not specifically limited, but it is preferable that weight of sulfur falls in a range of 0.002 to 0.1 times the weight of the unsaturated compound, and it is more preferable that the weight of sulfur falls in a range of 0.005 to 0.06 times the weight of the unsaturated compound. In the case where the usage of sulfur exceeds or falls short of the aforementioned range, a thiol compound may not be obtained at a high selectivity and a high yield. Sulfur reacts with the thiol compound in the system of reaction, thereby becoming polysulfide compounds such as disulfide compounds. Therefore, by using sulfur, the same effects as those in the case where polysulfide compounds are used can be achieved.

In the present invention, unclear is the reason why a reaction rate becomes higher while the selectivity and yield of the thiol compound are remarkably enhanced in the case where the nitrogen containing compound having a specific structure and the polysulfide compound expressed by the aforementioned formula (3) and/or sulfur are caused to coexist in the system of reaction, as compared with the case where only either of these compounds exists. However, it is presumed that in the system of reaction hydrogen sulfide and the polysulfide compound are remarkably activated by the nitrogen containing compound, thereby enhancing reactivity between hydrogen sulfide and the unsaturated compound.

Note that the combination of the nitrogen containing compound and the polysulfide compound and/or sulfur, and mixture ratios of these compounds are not particularly limited, but the mixture ratio of the nitrogen containing compound and the polysulfide compound (weight of the nitrogen containing compound/(weight of the nitrogen containing compound+weight of the polysulfide compound)) preferably falls in a range of 0.01 to 0.99, more preferably falls in a range of 0.05 to 0.95, and further more preferably falls in a range of 0.1 to 0.9. Besides, sulfur reacts with the thiol compound in the system of reaction, to be converted into a polysulfide compound such as a disulfide compound. Therefore, in the case where sulfur is caused to coexist, it is dealt with in the same manner as in the case where the polysulfide compound of an amount corresponding to the sulfur is caused to coexist.

Figure 1:
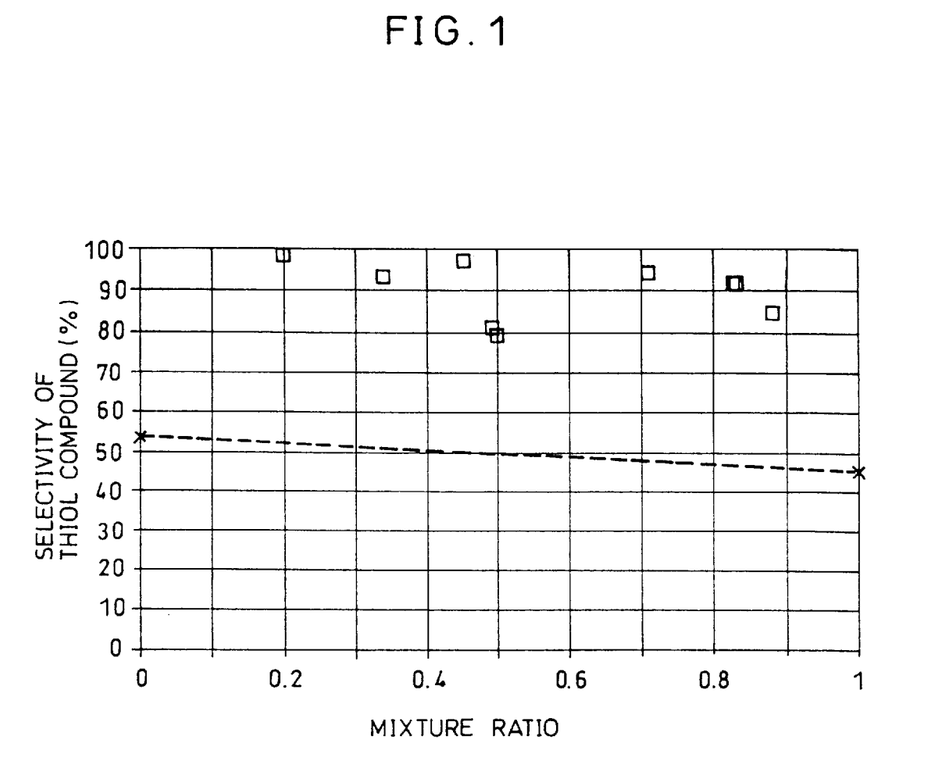
FIG. 1 is a graph of a multiplier effect which is achieved by causing a nitrogen containing compound and a polysulfide compound to coexist in a system of reaction.

The multiplier effects which are achieved by causing the nitrogen containing compound and the polysulfide compound to coexist in the system of reaction will be explained in the following description, with reference to the graph of FIG. 1. In the graph, the horizontal axis indicates mixture ratios of the nitrogen containing compound and the polysulfide compound (weight of the nitrogen containing compound/(weight of the nitrogen containing compound+weight of the polysulfide compound)). Therefore, the mixture ratio is 0 in the case where only the polysulfide compound is used, whereas the mixture ratio is 1 in the case where only the nitrogen containing compound is used. In the case where the nitrogen containing compound and the polysulfide compound are used at a weight ratio of 1:1, the mixture ratio is 0.5. The vertical axis indicates the selectivity (percent) of the thiol compound.

As clear from the graph, in the case where only the polysulfide compound is used and in the case where only the nitrogen containing compound is used, the selectivity of the thiol compound is about 50 percent. On the other hand, in the case where both the nitrogen containing compound and the polysulfide compound are used, that is, the method of the present invention is applied, the selectivity of the thiol compound is not less than 80 percent, as indicated by □, irrelevant to the mixture ratio. Thus, by causing the nitrogen containing compound and the polysulfide compound to coexist, the selectivity of the thiol compound is remarkably improved, as compared with the case where either of the compounds alone exists.

In the present invention, the unsaturated compound and hydrogen sulfide are caused to react, with the use of a catalyst. Any substance can be used as catalyst as far as it is a basic substance (basic catalyst), and any one of homogeneous and heterogeneous catalysts can be used. The following are examples of the catalysts: ammonia; organic amine compounds such as methylamine, ethylamine, propylamine, hexylamine, dimethylamine, trimethylamine, triethylamine, ethylenediamine, tetraethylenepentamine, triethylenediamine, and 1,8-diazalicyclo[5.4.0]-7-undecene; alkali metal alcoxides such as sodium methoxide, and sodium ethoxide; alkali metal hydroxides such as sodium hydroxide, and potassium hydroxide; anionic exchange resins; and inorganic solid bases. But, the catalyst of the present invention is not specifically limited. Examples of the inorganic solid base are: alkaline earth metal hydroxides such as magnesium hydroxide, and calcium hydroxide; alkaline earth metal oxides such as calcium oxide, strontium oxide, and barium oxide. One of these catalysts may be used alone, or an appropriate mixture of not less than two of them may be used. Ammonia and organic amine compounds are preferable since they have high catalytic activity.

The usage of the catalyst, though varying with a reaction method applied (described later), preferably falls in a range of 0.001 weight percent to 10 weight percent with respect to the unsaturated compound in the case where the catalyst is dissolved in the reactive solution, and more preferably falls in a range of 0.005 weight percent to 5 weight percent in the same case. In the case where the catalyst is an anionic exchange resin or an inorganic solid base, the usage of the same preferably falls in a range of 0.001 to 0.4 times the weight of the unsaturated compound, and more preferably 0.01 to 0.2 times. The catalytic activity is remarkably improved by causing the nitrogen containing compound and the polysulfide compound to coexist in the system of reaction. Therefore, the usage of the catalyst can be relatively reduced. In the case where the usage of the catalyst exceeds or falls short of the aforementioned range, it may possibly occur that the thiol compound cannot be obtained at a high selectivity and a high yield.

Note that the method for preparing the foregoing catalyst is not particularly specified. Besides, the catalyst may be carried on a carrier. Moreover, mechanical strength of the catalyst may be intensified by a molding promoter. Nothing is particularly preferred as the foregoing carrier or as the foregoing molding promotor, and any substances may be used as such, as long as they neither hinder the reaction nor lower the catalytic activity.

A reaction temperature is not particularly specified, and it may be set to any temperature. However, the reaction temperature preferably falls in a range of 0° C. to 150° C., and more preferably falls in a range of 20° C. to 100° C. In the case where the reaction temperature is lower than 0° C., the reaction rate is slowed down, thereby causing the reaction to take more time. This is not economical. Therefore, the thiol compound may not be efficiently produced. In the case where the reaction temperature exceeds 150° C., this likely causes decomposition of the thiol compound and secondly reaction of converting the thiol compound into sulfides, thereby lowering the yield of the thiol compound. In other words, the sequential reaction (secondary reaction) of the thiol compound, which is an object of the reaction, tends to occur, thereby producing by-products such as a sulfide compound, and as a result the yield of the thiol compound decreases. Moreover, since the reaction between the unsaturated compound and hydrogen sulfide is an exothermic reaction, it is desirable that heat is discharged from the system of reaction during the reaction. Note that the method for discharging the heat is not particularly specified.

A reaction pressure, though varying with the amount of hydrogen sulfide in the system of reaction and the reaction temperature, preferably falls in a range of 1 atm to 40 atm, and more preferably falls in a range of 1 atm to 20 atm. As the reaction pressure rises, more hydrogen sulfide is dissolved in the reactive solution, thereby accelerating the reaction. On the other hand, in this case, the reactor is required to have a structure with a greater breakdown strength, and this causes a disadvantage in that, for example, the device becomes bulkier. Therefore, the reaction pressure should be set, with the both aspects taken into consideration. Note that in the case where the reaction pressure exceeds 40 atm, an effect of acceleration of the reaction is less, whereas the device is made bulkier. Therefore, this is not preferable.

The reaction in the present invention may be carried out by any one among the batch method, the semi-batch method, and the continuous supply method. A method for mixing the unsaturated compound, hydrogen sulfide, the nitrogen containing compound, the polysulfide compound and/or sulfur, and the catalyst is not particularly specified, and various methods are applicable.

In the case where the batch method or the semi-batch method is used so as to cause the reaction, the ingredients are preferably mixed, for example, in the following manner: after the nitrogen containing compound, the polysulfide compound and/or sulfur, and the catalyst are put in the reactor, they are stirred while heated to a set temperature, that is, the reaction temperature, and then, hydrogen sulfide and the unsaturated compound are supplied thereto. The unsaturated compound may be put into the reactor before hydrogen sulfide is supplied thereto.

To supply hydrogen sulfide, a supply line equipped with a pressure adjusting device and the like may be provided to the reactor, so that hydrogen sulfide may be supplied to the reactor through the supply line, with the pressure adjusted to a desired set level. As a method for supplying hydrogen sulfide, for example, the following method may be taken: before the reaction starts, hydrogen sulfide is supplied to the reactor so that the pressure inside the reactor is at a desired set level, and after the reaction is caused to start with supply of the unsaturated compound, hydrogen sulfide is supplied thereto so as to make up for consumption due to the reaction so that the pressure inside the reactor is kept at the set level. In the case where the batch method or the semi-batch method is applied, supply of set amounts of hydrogen sulfide and the unsaturated compound is carried out during a set period of time, and the mixture is aged for a set period of time so that the reaction is completed.

In the case where the continuous supply method is applied, the supply is preferably carried out in the following manner: hydrogen sulfide, the unsaturated compound, the nitrogen containing compound, the polysulfide compound and/or sulfur, and the catalyst are continuously supplied to the reactor, such as a reaction tube, which is set to a predetermined pressure and a predetermined temperature. The above hydrogen sulfide, unsaturated compound, nitrogen containing compound, polysulfide compound and/or sulfur, and the catalyst may be individually supplied to the reactor. Alternatively, some of them may be previously mixed, and then, supplied to the reactor. In the case where the catalyst is a solid substance such as an anionic exchange resin or an inorganic solid base, hydrogen sulfide, the unsaturated compound, the nitrogen containing compound, and the polysulfide compound and/or sulfur may be supplied after the catalyst is placed in the reactor. Note that a liquid hourly space velocity (LHSV) of the reactive solution which passes through the reaction container is not particularly limited.

The thiol compound is separated from the reactive solution after the reaction is completed, by a simple operation such as filtering or distillation.

As has been described so far, according to the manufacturing method in accordance with the present invention whereby the nitrogen containing compound and the polysulfide compound are caused to coexist in the system of reaction, (1) the unsaturated compound such as an unsaturated ester or an unsaturated acid and (2) hydrogen sulfide can be caused to react smoothly, and the thiol compound can be obtained at a high selectivity and a high yield, as compared with the case where only either the nitrogen containing compound or the polysulfide compound and/or sulfur exists in the system of reaction. In other words, in comparison with the above cases, the selectivity and the yield of the thiol compound can be remarkably improved.

The following examples and comparative examples will explain the present invention in more detail. However, these examples do not limit the scope of the present invention.

Note that a conversion ratio of the unsaturated compound which is expressed by the formula (1) and a selectivity of the thiol compound which is expressed by the formula (2) are defined as follows.

CONVERSION RATIO OF UNSATURATED COMPOUND (%) =

$$\frac{\text{(NUMBER OF MOLES OF CONSUMED UNSATURATED COMPOUND)}}{\text{(NUMBER OF MOLES OF SUPPLIED UNSATURATED COMPOUND)}} \times 100$$

SELECTIVITY OF THIOL COMPOUND (%) =

$$\frac{\text{(NUMBER OF MOLES OF THIOL COMPOUND)}}{\text{(NUMBER OF MOLES OF THIOL COMPOUND)} + \text{(NUMBER OF MOLES OF SULFIDE COMPOUND/2)}} \times 100$$

Note that the sulfide compound is expressed by a following formula (4):

$$S + CH_2 - CHR^1 - COOR^2)_2 \quad (4)$$

where $R^1$ represents a hydrogen atom or a methyl group, and $R^2$ represents a hydrogen atom or a hydrocarbon group with 1 to 18 carbon atoms. The sulfide compound is a by-product which is by-produced by secondary reaction of the thiol compound as the target substance.

In the case where ammonia was used as a catalyst in the following examples and the comparative examples, a 28 weight percent ammonia water solution was used. Therefore, an amount of ammonia mentioned in the examples and the comparative examples is a reduced value as pure ammonia.

[EXAMPLE 1]

As the reaction container (reactor), a 100 ml autoclave was used. In the autoclave, 20.3 g of methyl acrylate (hereinafter referred to as MA) as the unsaturated compound, 20.1 g of 1,3-dimethyl-2-imidazolidinone (hereinafter referred to as DMI) as the nitrogen containing compound, 24.4 g of methyl dithiodipropionate (hereinafter referred to as DTD) as the polysulfide compound, and 0.0071 g of ammonia as the catalyst were supplied.

Then, the autoclave was filled with nitrogen gas, and it was sealed. While the reactive solution was stirred at a temperature of the freezing point, 10.4 g of hydrogen sulfide was supplied thereto. Hydrogen sulfide was smoothly dissolved in the reactive solution, and the pressure inside the autoclave (initial pressure) becomes 3.5 kg/cm$^2$ (gauge pressure). A molar ratio for hydrogen sulfide and MA (hydrogen sulfide/MA) was 1.3. The autoclave was cooled down with the use of ice water.

After the supply of hydrogen sulfide, the reaction was started by heating the system of reaction to 40° C., and this temperature was kept for 4 hours for the reaction. Thereafter hydrogen sulfide was purged out of the autoclave, and the autoclave was cooled down. The pressure inside the autoclave at the point when the reaction was completed (reaction end pressure) was 3.0 kg/cm$^2$ (gauge pressure).

The reactive solution thus obtained was taken out and analyzed with a gas chromatography (GC). As a result, the conversion ratio of MA was 100 percent, while the selectivity of methyl-3-mercapto-propionate (hereinafter referred to as MMP) as the thiol compound was 97.5 percent. The reaction conditions and the result of the reaction are shown in Tables 1 and 2.

[EXAMPLES 2 through 16]

Using the same reactor as that in Example 1, the same operations as those in Example 1 were conducted so that the same reaction as that in Example 1 took place. Reaction conditions and results of these examples are shown in Tables 1 through 6, in the same manner as that in Example 1.

[COMPARATIVE EXAMPLE 1]

A reaction was caused without the polysulfide compound. To be more specific, in the same autoclave as that of Example 1, 20.2 g of MA, 20.2 g of DMI, and 0.0052 g of ammonia were supplied.

Then, the autoclave was filled with nitrogen gas, and it was sealed. While the reactive solution was stirred at a temperature of the freezing point, 10.6 g of hydrogen sulfide was supplied thereto. The pressure inside the autoclave was 3.2 kg/cm$^2$ (gauge pressure). A molar ratio for hydrogen sulfide and MA was 1.3. The autoclave was cooled down with the use of ice water.

After the supply of hydrogen sulfide, the reaction was started by heating the system of reaction to 40° C., and this temperature was kept for 3 hours for the reaction. Thereafter hydrogen sulfide was purged out of the autoclave, and the autoclave was cooled down. The pressure inside the autoclave at the point when the reaction was completed was 5.0 kg/cm$^2$ (gauge pressure).

The reactive solution thus obtained was taken out and analyzed in the same manner as in Example 1. As a result, the conversion ratio of MA was 100 percent, but the selectivity of MMP was as low as 44.5 percent. The reaction conditions and the result of the reaction are shown in Tables 5 and 6.

[COMPARATIVE EXAMPLE 2]

A reaction was caused without the nitrogen containing compound. To be more specific, in the same autoclave as that of Example 1, 20.0 g of MA, 24.0 g of DTD, and 0.0059 g of ammonia were supplied.

Then, the autoclave was filled with nitrogen gas, and it was sealed. While the reactive solution was stirred at a temperature of the freezing point, 10.4 g of hydrogen sulfide was supplied thereto. The pressure inside the autoclave was 4.3 kg/cm² (gauge pressure). A molar ratio for hydrogen sulfide and MA was 1.3. The autoclave was cooled down with the use of ice water.

After the supply of hydrogen sulfide, the reaction was started by heating the system of reaction to 40° C., and this temperature was kept for 3 hours for the reaction. Thereafter hydrogen sulfide was purged out of the autoclave, and the autoclave was cooled down. The pressure inside the autoclave at the point when the reaction was completed was 10.0 kg/cm² (gauge pressure).

The reactive solution thus obtained was taken out and analyzed in the same manner as in Example 1. As a result, the conversion ratio of MA was as low as 31.4 percent, and the selectivity of MMP was as low as 54.0 percent. The reaction conditions and the result of the reaction are shown in Tables 5 and 6.

[COMPARATIVE EXAMPLE 3]

A reaction was caused, by using methyl alcohol instead of the nitrogen containing compound. To be more specific, in the same autoclave as that of Example 1, 20.2 g of MA, 20.2 g of methyl alcohol, 4.0 g of DTD, and 0.0053 g of ammonia were supplied.

Then, the autoclave was filled with nitrogen gas, and it was sealed. While the reactive solution was stirred at a temperature of the freezing point, 10.6 g of hydrogen sulfide was supplied thereto. The pressure inside the autoclave was 4.0 kg/cm² (gauge pressure). A molar ratio for hydrogen sulfide and MA was 1.3. The autoclave was cooled down with the use of ice water.

After the supply of hydrogen sulfide, the reaction was started by heating the system of reaction to 40° C., and this temperature was kept for 4.5 hours for the reaction. Thereafter hydrogen sulfide was purged out of the autoclave, and the autoclave was cooled down. The pressure inside the autoclave at the point when the reaction was completed was 6.0 kg/cm² (gauge pressure).

The reactive solution thus obtained was taken out and analyzed in the same manner as in Example 1. As a result, the conversion ratio of MA was as low as 62.6 percent, and the selectivity of MMP was as low as 67.1 percent. The reaction conditions and the result of the reaction are shown in Tables 5 and 6.

TABLE 1

|  | UNSATURATED COMPOUND (g) | HYDROGEN SULFIDE (g) | NITROGEN CONT. COMPOUND (g) | DTD (g) | CATALYST (g) | REACTION TEMP. (°C.) | REACTION PERIOD (hr) |
|---|---|---|---|---|---|---|---|
| EX. 1 | MA 20.3 | 10.4 | DMI 20.1 | 24.4 | AMMONIA 0.0071 | 40 | 4 |
| EX. 2 | MA 20.1 | 9.8 | DMI 20.4 | 8.4 | AMMONIA 0.0066 | 40 | 2 |
| EX. 3 | MA 20.1 | 10.3 | DMI 20.2 | 4.1 | AMMONIA 0.0056 | 40 | 4.5 |
| EX. 4 | MA 20.3 | 10.4 | DMI 20.2 | 2.7 | AMMONIA 0.0053 | 40 | 3 |
| EX. 5 | MA 20.0 | 10.1 | DMI 20.2 | 24.0 | SODIUM HYDROXIDE 0.0080 | 40 | 3.5 |
| EX. 6 | MA 19.9 | 10.4 | DMI 4.0 | 16.0 | TRIETHYL AMINE 0.0650 | 40 | 4 |
| EX. 7 | MA 20.1 | 10.4 | DMF 20.0 | 4.2 | AMMONIA 0.0061 | 40 | 3 |

DTD: methyl dithiodipropionate
MA: methyl acrylate
DMI: 1,3-dimethyl-2-imidazolidinone
DMF: N,N-dimethyl formamide

TABLE 2

|  | REACTION PRESSURE (kg/cm²) | | MOLAR RATIO* | CONVERSION RATIO** (%) | SELECTIVITY OF THIOL COMPOUND (%) |
|---|---|---|---|---|---|
|  | INITIAL PRESSURE | END PRESSURE | | | |
| EX. 1 | 3.5 | 3.0 | 1.3 | MA 100 | 97.5 |
| EX. 2 | 3.2 | 2.9 | 1.2 | MA 100 | 94.2 |
| EX. 3 | 3.0 | 3.0 | 1.3 | MA 100 | 91.6 |
| EX. 4 | 2.0 | 2.0 | 1.3 | MA 100 | 84.6 |
| EX. 5 | 3.0 | 2.5 | 1.3 | MA 100 | 97.9 |
| EX. 6 | 2.5 | 3.0 | 1.3 | MA 100 | 98.7 |
| EX. 7 | 2.9 | 3.0 | 1.3 | MA 100 | 91.4 |

MA: methyl acrylate
MOLAR RATIO*: molar ratio for hydrogen sulfide and unsaturated compound
CONVERSION RATIO**: conversion ratio of unsaturated compound

TABLE 3

| | UNSATURATED COMPOUND (g) | HYDROGEN SULFIDE (g) | NITROGEN CONT. COMPOUND (g) | DTD (g) | CATALYST (g) | REACTION TEMP. (°C.) | REACTION PERIOD (hr) |
|---|---|---|---|---|---|---|---|
| EX. 8 | MA 29.1 | 14.1 | DMF 5.8 | 5.8 | AMMONIA 0.0072 | 40 | 3 |
| EX. 9 | MA 28.5 | 14.6 | NMPD 5.7 | 5.8 | AMMONIA 0.0070 | 40 | 3 |
| EX. 10 | MA 20.1 | 9.8 | DMI 20.1 | (SULFUR) 0.5 | AMMONIA 0.0051 | 40 | 3 |
| EX. 11 | MA 20.0 | 9.6 | DMI 4.1 | 15.9 | IRA94S 0.230 | 40 | 3 |
| EX. 12 | MA 19.9 | 10.3 | NMPD 4.0 | 15.9 | TRI-METHYL-AMINE 0.0182 | 40 | 4 |
| EX. 13 | MAEH 20.0 | 5.0 | DMI 19.9 | (SULFUR) 0.5 | TRI-ETHYL-AMINE 0.698 | 40 | 3.5 |

DTD: methyl dithiodipropionate
MA: methyl acrylate
MAEH: 2-ethylhexyl methacrylate
DMF: N,N-dimethyl formamide
NMPD: N-methyl-2-pyrrolidone
DMI: 1,3-dimethyl-2-imidazolidinone
IRA94S: weak basic anionic exchange resin (produced by Rohm & Haas Co.)

TABLE 4

| | REACTION PRESSURE (kg/cm$^2$) | | MOLAR RATIO* | CONVERSION RATIO** (%) | SELECTIVITY OF THIOL COMPOUND (%) |
|---|---|---|---|---|---|
| | INITIAL PRESSURE | END PRESSURE | | | |
| EX. 8 | 5.0 | 4.5 | 1.2 | MA 100 | 79.1 |
| EX. 9 | 5.0 | 4.5 | 1.3 | MA 100 | 80.6 |
| EX. 10 | 3.1 | 3.0 | 1.2 | MA 100 | 92.5 |
| EX. 11 | 3.2 | 3.0 | 1.2 | MA 100 | 94.2 |
| EX. 12 | 3.0 | 3.2 | 1.3 | MA 100 | 98.0 |
| EX. 13 | 1.7 | 2.0 | 1.3 | MAEH 100 | 93.7 |

MA: methyl acrylate
MOLAR RATIO*: molar ratio for hydrogen sulfide and unsaturated compound
CONVERSION RATIO**: conversion ratio of unsaturated compound

TABLE 5

| | UNSATURATED COMPOUND (g) | HYDROGEN SULFIDE (g) | NITROGEN CONT. COMPOUND (g) | DTD (g) | CATALYST (g) | REACTION TEMP. (°C.) | REACTION PERIOD (hr) |
|---|---|---|---|---|---|---|---|
| EX. 14 | MA 20.0 | 10.3 | NMPD 4.0 | 15.9 | AMMONIA 0.0043 | 40 | 3 |
| EX. 15 | MA 20.0 | 9.9 | NMPD 4.0 | 16.1 | TEPA 0.0132 | 40 | 3.5 |
| EX. 16 | MA 20.0 | 10.0 | NMPD 4.0 | 16.1 | DBU 0.0062 | 44 | 4 |
| COMP. EX. 1 | MA 20.2 | 10.6 | DMI 20.2 | / | AMMONIA 0.0052 | 40 | 3 |
| COMP. EX. 2 | MA 20.0 | 10.4 | / | 24.0 | AMMONIA 0.0059 | 40 | 3 |
| COMP. EX. 3 | MA 20.2 | 10.6 | (METHYL ALCOHOL) 20.2 | 4.0 | AMMONIA 0.0053 | 40 | 4.5 |

DTD: methyl dithiodipropionate
MA: methyl acrylate
NMPD: N-methyl-2-pyrrolidone
DMI: 1,3-dimethyl-2-imidazolidinone
TEPA: tetraethylenepentamine
DBU: 1,8-diazabicyclo[5.4.0]-7-undecene

TABLE 6

| | REACTION PRESSURE (kg/cm²) | | | CON-VERSION | SELECTIVITY OF THIOL COM- |
|---|---|---|---|---|---|
| | INITIAL PRESSURE | END PRESSURE | MOLAR RATIO* | RATIO** (%) | POUND (%) |
| EX. 14 | 3.7 | 4.4 | 1.3 | MA 100 | 95.7 |
| EX. 15 | 4.5 | 3.5 | 1.3 | MA 100 | 97.3 |
| EX. 16 | 4.5 | 3.0 | 1.3 | MA 100 | 98.1 |
| COMP. EX. 1 | 3.2 | 5.0 | 1.3 | MA 100 | 44.5 |
| COMP. EX. 2 | 4.3 | 10.0 | 1.3 | MA 31.4 | 54.0 |
| COMP. EX. 3 | 4.0 | 6.0 | 1.3 | MA 62.6 | 67.1 |

MA: methyl acrylate
MOLAR RATIO*: molar ratio for hydrogen sulfide and unsaturated compound
CONVERSION RATIO**: conversion ratio of unsaturated compound

[EXAMPLE 17]

As the reaction container (reactor), a 300 ml autoclave equipped with a dropping device was used. In order to continuously supply hydrogen sulfide to the autoclave, a supply line equipped with a pressure adjusting device was provided to the autoclave. In the autoclave, 60.1 g of DMI, 12.1 g of DTD, and 0.0171 g of ammonia were supplied.

Thereafter, the autoclave was filled with nitrogen gas, and it was sealed. While the reactive solution was stirred, it was heated to 40° C. Then, hydrogen sulfide was supplied to the autoclave through the supply line so that the pressure inside the autoclave became 5.0 atm. 60.0 g of MA was supplied thereto during 4 hours, while the temperature was kept at 40° C. During this period, hydrogen sulfide was continuously supplied so that the pressure inside the autoclave was kept constant (5.0 atm).

After the supply of MA, the supply of hydrogen sulfide was suspended, and the reactive solution was aged for 0.5 hour at a temperature of 40° C. so that the reaction was completed. A total amount of hydrogen sulfide supplied to the autoclave was 38.8 g. A molar ratio for hydrogen sulfide and MA was 1.6.

Thereafter hydrogen sulfide was purged out of the autoclave, and the autoclave was cooled down. The reactive solution thus obtained was taken out and analyzed in the same manner as in Example 1. As a result, the conversion ratio of MA was 100 percent, while the selectivity of MMP was 91.4 percent. The reaction conditions and the result of the reaction are shown in Tables 7 and 8.

[EXAMPLES 18 and 19]

Using the same reactor as that in Example 17, the same operations as those in Example 17 were conducted so that the same reaction to that in Example 17 took place. Reaction conditions and results of these examples are shown in Tables 7 and 8, in the same manner as that in Example 1.

TABLE 7

| | UNSATURATED COMPOUND (g) | HYDROGEN SULFIDE (g) | NITROGEN CONT. COMPOUND (g) | DTD (g) | CATALYST (g) | REACTION TEMP. (°C.) | REACTION PERIOD (hr) |
|---|---|---|---|---|---|---|---|
| EX. 17 | MA 60.0 | 38.8 | DMI 60.1 | 12.1 | AMMONIA 0.0171 | 40 | 4.0 |
| EX. 18 | MA 58.0 | 30.0 | DMI 60.1 | 12.2 | AMMONIA 0.0164 | 40 | 3.7 |
| EX. 19 | MA 82.9 | 55.0 | DMI 16.0 | 32.0 | AMMONIA 0.0222 | 40 | 3.0 |

DTD: methyl dithiodipropionate
MA: methyl acrylate
DMI: 1,3-dimethyl-2-imidazolidinone

TABLE 8

| | AGING PERIOD (hr) | REACTION PRESSURE (kg/cm²) | MOLAR RATIO* | CONVERSION RATIO** (%) | SELECTIVITY OF THIOL COMPOUND (%) |
|---|---|---|---|---|---|
| EX. 17 | 0.5 | 5.0 | 1.6 | MA 100 | 91.4 |
| EX. 18 | 0.5 | 3.0 | 1.3 | MA 100 | 84.3 |
| EX. 19 | 1.5 | 8.8 | 1.7 | MA 100 | 92.3 |

MA: methyl acrylate
MOLAR RATIO*: molar ratio for hydrogen sulfide and unsaturated compound
CONVERSION RATIO**: conversion ratio of unsaturated compound As clear from the results of Examples 1 through 19, the thiol compound can be obtained at a high selectivity in the case where the manufacturing method of the present invention is applied, even though the molar ratio for hydrogen sulfide and the unsaturated compound (hydrogen sulfide/unsaturated compound) is relatively low. In other words, an amount of sulfide compounds which are produced as by-products is relatively small. In contrast, as clear form the results of Comparative Example 1, the thiol compound cannot be obtained at a high selectivity in the case where the nitrogen containing compound is solely used. Besides, as clear from the results of Comparative Example 2, both the conversion ratio of the unsaturated compound and the selectivity of the thiol compound are low in the case where the polysulfide compound is solely used. Furthermore, as clear from the results of Comparative Example 3, both the conversion ratio of the unsaturated compound and the selectivity of the thiol compound are low in the case where (1) a compound other than the nitrogen containing compound and (2) the polysulfide compound coexist.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The method of the present invention for manufacturing a thiol compound comprises the step of causing reaction between an unsaturated compound and hydrogen sulfide so as to produce the thiol compound, the unsaturated compound and the thiol compound being expressed by following formulas (1) and (2), respectively:

$$CH_2=CR^1-COOR^2 \quad (1)$$

$$HS-CH_2-CHR^1-COOR^2 \quad (2)$$

where $R^1$ represents a hydrogen atom or a methyl group, and $R^2$ represents a hydrogen atom or a hydrocarbon group with 1 to 18 carbon atoms, wherein (i) at least one nitrogen containing compound which is selected from the group consisting of amide compounds each having an amide group without a substituent, amide compounds each having an amide group whose nitrogen atom has a substituent hydrocarbon group with 1 to 6 carbon atoms, urea compounds each having an ureylene group without a substituent, and urea compounds in each of which at least one of two nitrogen atoms (N, N') has a substituent hydrocarbon group with 1 to 6 carbon atoms, and (ii) either a polysulfide compound or sulfur, or the both, coexist in a system of reaction, the polysulfide compound being expressed by a following formula (3):

$$R^4OOC-CHR^3-CH_2-S_x-CH_2-CHR^3-COOR^4 \quad (3)$$

where $R^3$ represents a hydrogen atom or a methyl group, $R^4$ represents a hydrogen atom or a hydrocarbon group with 1 to 18 carbon atoms, and x represents an integral number of 2 to 5.

With this method, (1) the unsaturated compound such as an unsaturated ester or an unsaturated acid and (2) hydrogen sulfide are caused to smoothly react with each other, and the thiol compound, which is the object to be obtained, can be obtained at a high selectivity and a high yield, as compared with the case where only either the nitrogen containing compound, or the polysulfide compound and/or sulfur, is supplied to the system of reaction. In short, as compared with this case, an effect that the selectivity and the yield of the thiol compound can be remarkably improved is achieved. The thiol compounds are chemical substances of great use which are widely utilized as material of pharmaceutical products, agricultural chemicals, and various kinds of industrial chemical products.

We claim:

1. A method for manufacturing a thiol compound, said method comprising the step of:

causing reaction between an unsaturated compound and hydrogen sulfide so as to produce said thiol compound, said unsaturated compound and said thiol compound being expressed by following formulas (1) and (2), respectively:

$$CH_2=CR^1-COOR^2 \quad (1)$$

$$HS-CH_2-CHR^1-COOR^2 \quad (2)$$

where $R^1$ represents a hydrogen atom or a methyl group, and $R^2$ represents a hydrogen atom or a hydrocarbon group with 1 to 18 carbon atoms, wherein (i) at least one nitrogen containing compound which is selected from the group consisting of amide compounds each having an amide group without a substituent, amide compounds each having an amide group whose nitrogen atom has a substituent hydrocarbon group with 1 to 6 carbon atoms, urea compounds each having an ureylene group without a substituent, and urea compounds in each of which at least one of two nitrogen atoms (N, N') has a substituent hydrocarbon group with 1 to 6 carbon atoms, and (ii) either a polysulfide compound or sulfur, or the both, coexist in a system of reaction, said polysulfide compound being expressed by a following formula (3):

$$R^4OOC-CHR^3-CH_2-S_x-CH_2-CHR^3-COOR^4 \quad (3)$$

where $R^3$ represents a hydrogen atom or a methyl group, $R^4$ represents a hydrogen atom or a hydrocarbon group with 1 to 18 carbon atoms, and x represents an integral number of 2 to 5.

2. The method as set forth in claim 1, wherein x in the formula (3) is 2.

3. The method as set forth in claim 1, wherein $R^3$ in the formula (3) is equal to $R^1$, and $R^4$ in the formula (3) is equal to $R^2$.

4. The method as set forth in claim 1, wherein said unsaturated compound is acrylic ester.

5. The method as set forth in claim 1, wherein a usage of said hydrogen sulfide is in a range of 1.0 mole to 5.0 mole with respect to 1 mole of said unsaturated compound.

6. The method as set forth in claim 1, wherein (i) said nitrogen containing compound with a weight in a range of 0.01 to 5 times a weight of said unsaturated compound, and (ii) either said polysulfide compound with a weight in a range of 0.02 to 5 times the weight of said unsaturated compound, or said sulfur with a weight in a range of 0.002 to 0.1 time the weight of said unsaturated compound, or the both, coexist in the system of reaction.

7. The method as set forth in claim 1, wherein a mixture ratio for said nitrogen containing compound and said polysulfide compound is in a range of 0.01 to 0.99, the mixture ratio being defined as:

$$\text{mixture ratio} = \frac{\text{a weight of said nitrogen containing compound}}{\text{a weight of said nitrogen containing compound} + \text{a weight of said polysulfide compound}}$$

8. The method as set forth in claim 1, wherein the reaction is caused under the presence of a basic catalyst.

9. The method as set forth in claim 8, wherein said basic catalyst is composed of at least one selected from the group consisting of ammonia and organic amine compounds.

10. The method as set forth in claim 8, wherein said basic catalyst is a homogeneous catalyst, and a usage of said basic catalyst is in a range of 0.001 percent by weight to 10 percent by weight with respect to said unsaturated compound.

11. The method as set forth in claim 8, wherein said basic catalyst is a heterogeneous catalyst, and a usage of said basic catalyst is in a range of 0.001 to 0.4 times the weight of said unsaturated compound.

12. The method as set forth in claim 1, wherein a reaction temperature is in a range of 0° C. to 150° C.

13. The method as set forth in claim 1, wherein a reaction pressure is in a range of 1 atm to 40 atm.

* * * * *